US 6,679,982 B1

(12) United States Patent
Matsuzaki et al.

(10) Patent No.: US 6,679,982 B1
(45) Date of Patent: Jan. 20, 2004

(54) OXYGEN SENSOR

(75) Inventors: Hiroshi Matsuzaki, Iwakura (JP); Keiji Suzuki, Inuyama (JP); Teppei Ookawa, Kounan (JP); Hiroshi Kubota, Wako (JP); Seiichi Hosogai, Wako (JP); Hiroyuki Fujita, Wako (JP); Katsunori Nakamura, Wako (JP)

(73) Assignees: NGK Spark Plug Co., Ltd., Aichi (JP); Honda Motor Co., Ltd., Tokyo (JP)

( * ) Notice: Subject to any disclaimer, the term of this patent is extended or adjusted under 35 U.S.C. 154(b) by 172 days.

(21) Appl. No.: 09/671,591

(22) Filed: Sep. 28, 2000

Related U.S. Application Data

(63) Continuation of application No. 09/130,646, filed on Aug. 7, 1998, now abandoned.

(30) Foreign Application Priority Data

Aug. 7, 1997 (JP) .............................. 9-213499
Jan. 29, 1998 (JP) .............................. 10-17270

(51) Int. Cl.$^7$ ............................................. G01N 27/407
(52) U.S. Cl. .................. 204/424; 204/292; 204/428; 204/429; 427/123; 427/125; 427/383.5
(58) Field of Search .................. 204/421–429, 204/292, 293; 427/383.5

(56) References Cited

U.S. PATENT DOCUMENTS

| | | | |
|---|---|---|---|
| 3,843,400 A | 10/1974 | Radford et al. | 204/421 |
| 3,941,673 A | 3/1976 | Takao et al. | 204/195 S |
| 3,981,785 A | 9/1976 | Sandler | 204/195 S |
| 4,021,326 A | 5/1977 | Pollner et al. | 204/429 |
| 4,049,524 A | 9/1977 | Togawa et al. | 204/195 S |
| 4,107,019 A | 8/1978 | Takao et al. | 204/195 S |
| 4,159,353 A | 6/1979 | Adelsberg et al. | 427/383.5 |
| 4,170,530 A | 10/1979 | Watanabe et al. | 204/421 |
| 4,177,112 A | 12/1979 | Suzuki et al. | 204/429 |
| 4,225,634 A | 9/1980 | Tanaka et al. | 427/283.5 |
| 4,340,618 A | 7/1982 | Fury et al. | 427/383.5 |
| 4,476,008 A | 10/1984 | Sano et al. | 204/429 |
| 4,477,487 A | 10/1984 | Kojima et al. | 427/383.5 |
| 5,326,597 A | 7/1994 | Sawada et al. | 427/448 |
| 5,443,711 A | 8/1995 | Kojima et al. | 204/429 |
| 5,472,580 A | 12/1995 | Kennard et al. | 204/424 |
| 5,472,591 A | 12/1995 | Saito et al. | 204/429 |
| 5,716,507 A | 2/1998 | Tanaka et al. | 204/429 |

FOREIGN PATENT DOCUMENTS

| | | | |
|---|---|---|---|
| EP | 0 331 050 | 9/1989 | ......... G01N/278/56 |
| JP | 50-14396 | 2/1975 | |
| JP | 53-50888 | 5/1978 | ......... G01N/27/58 |
| JP | 54-89686 | 7/1979 | ......... G01N/27/58 |
| JP | 9-236575 | 9/1997 | ......... G01N/27/409 |

OTHER PUBLICATIONS

Patent Abstracts of Japan, vol. 097, No. 012, Dec. 25, 1997 & JP 09 203719 A (Yazaki Corp.; Osaka Gas Co., LTD.) Aug. 5, 1997 *Abstract.

Haaland D M: "Noncatalytic electrodes for solid–electrolyte oxygen sensors", Journal of the Electrochemical Society, Apr. 1980, USA vol. 127, No. 4 pp 796–804, XP002084798 ISSN 0013–4651 pp. 796–804.

Primary Examiner—T. Tung
(74) Attorney, Agent, or Firm—Sughrue Mion, PLLC

(57) ABSTRACT

An oxygen sensor is disposed downstream from a catalyst for purifying exhaust gas from an internal combustion engine and which can suppress an influence of unburnt hydrocarbon on an output voltage. After forming a platinum thin film on the outer periphery of a zirconia ceramic body, only a detection electrode of the ceramic body is dipped in a silver nitrate aqueous solution of 0.1 mol/l, and the silver nitrate is pyrolyzed through a heat treatment. Subsequently, a platinum reference electrode is formed on the inner periphery of the ceramic body. To protect the silver-doped detection electrode, a protective layer is formed on the surface of the detection electrode. By the exposure to combustion gas and through aging, a detection element is formed, and set into a metal case together with a cylindrical heater, to complete an oxygen sensor to be disposed downstream from a CNG engine catalyst.

16 Claims, 5 Drawing Sheets

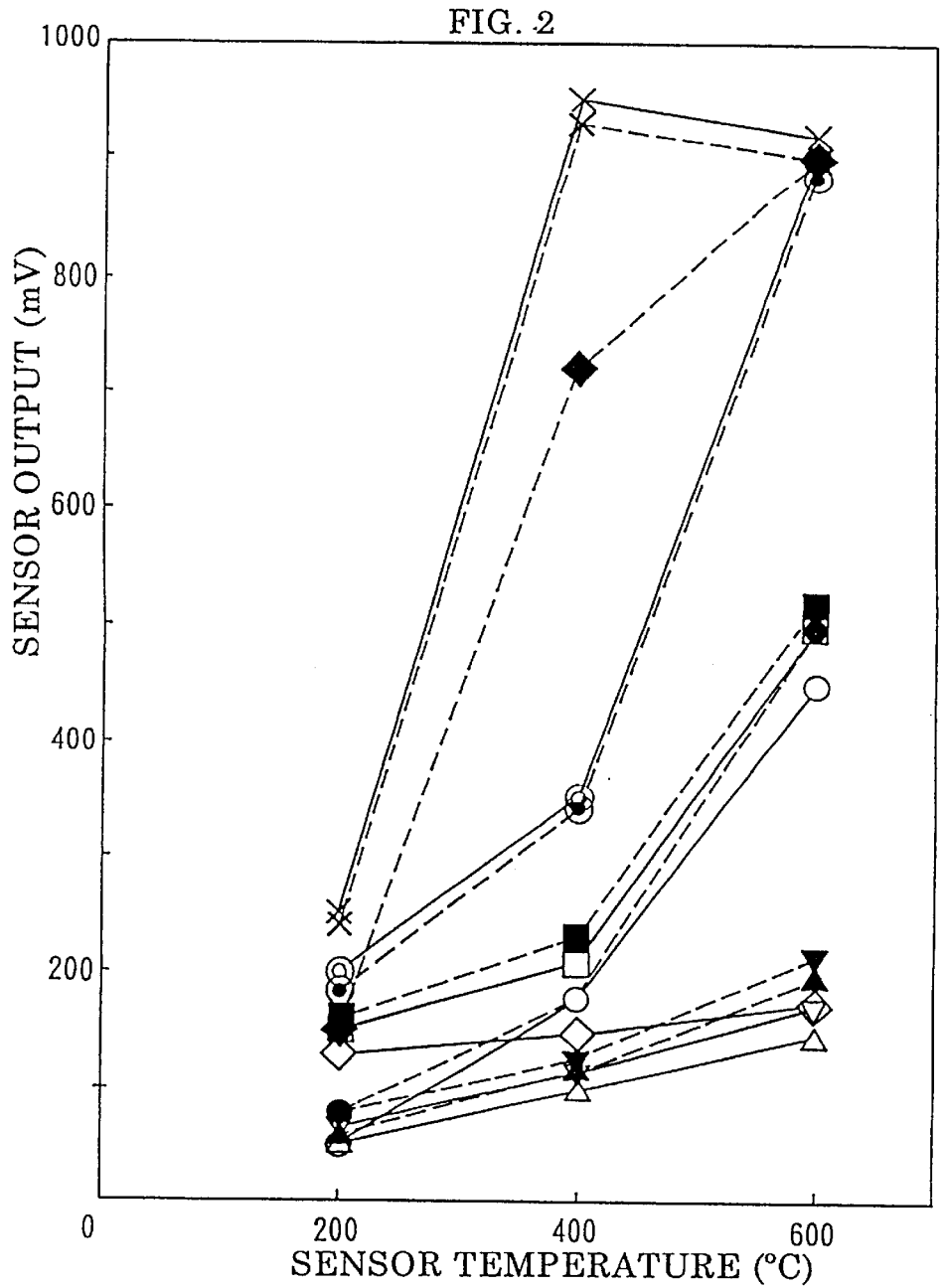

WHEN CATALYST IS NORMAL:

WHEN CATALYST IS DETERIORATED:

WHEN UNBURNT METHANE IS BURNT:

WHEN CATALYST IS NORMAL:

WHEN CATALYST IS DETERIORATED:

— — — OXYGEN SENSOR BEFORE CATALYST
———— OXYGEN SENSOR BEHIND CATALYST

OXYGEN SENSOR

This is a Continuation of application Ser. No. 09/130,646 filed Aug. 7, 1998, now abandoned, the disclosure of which is incorporated herein by reference.

FIELD OF THE INVENTION

The present invention relates to sensors, and more particularly to oxygen sensors.

BACKGROUND OF THE INVENTION

As a measure of the purifying capability of a catalyst for purifying exhaust gas from a gasoline engine (hereinafter referred to as the catalyst), the oxygen storage capability of the catalyst has been heretofore noted. It is known that the deterioration degree of the catalyst is estimated by measuring the oxygen storage capability with an oxygen sensor. The deterioration degree is the amount by which a catalyst has deteriorated, that is, by how much it has lost its effectiveness, from use over time. Examples of a method of detecting the catalyst deterioration include the following:
First Catalyst Deterioration Detecting Method For example, in a case where an air/fuel ratio is controlled, via a carburetor or fuel injector, or by addition/reduction of air via a catalyst air pump, based on an output of an oxygen sensor disposed downstream from the catalyst, the deterioration degree of the catalyst can be estimated based on the output of the oxygen sensor. Note that the output voltage is inversely proportional to the oxygen at the sensor.

Specifically, as shown in FIG. 3A, at a time when the voltage output of the oxygen sensor downstream from the catalyst rises, the air/fuel ratio is controlled toward a lean side. At a time when the output of the oxygen sensor falls, the air/fuel ratio is controlled toward a rich side. Here, when the purifying efficiency of the catalyst is high, even if the air/fuel ratio is controlled toward the lean side when the output of the oxygen sensor downstream from the catalyst rises, the oxygen storage capability of the catalyst is high, so that oxygen is stored. Therefore, the output voltage of the oxygen sensor downstream from the catalyst still remains high. The output voltage does not drop until oxygen is sufficiently stored. Subsequently, when the output voltage lowers, the air/fuel ratio is controlled to the rich side. Since the stored oxygen is consumed, the output voltage of the oxygen sensor downstream from the catalyst still remains low. The output voltage does not increase until the stored oxygen is consumed. As aforementioned, when the purifying efficiency of the catalyst is high, a reversing time, i.e., a high-output keeping time plus a low-output keeping time is lengthened. When the purifying efficiency of the catalyst is lowered, however, the oxygen storage capability of the catalyst is lowered. Therefore, the reversing time is shortened as shown in FIG. 3B. Therefore, the deterioration degree of the catalyst can be detected by tracing the output voltage of the oxygen sensor downstream from the catalyst and judging whether the reversing time is long or short.
Second Catalyst Deterioration Detecting Method In a case where the air/fuel ratio is controlled based on an output of an oxygen sensor disposed upstream of the catalyst, the deterioration degree of the catalyst is estimated based on an output of an oxygen sensor disposed downstream of the catalyst.

Specifically, when the purifying efficiency of the catalyst is high, the oxygen storage capability of the catalyst is high. Therefore, the change of the air/fuel ratio toward the rich/lean side in the exhaust gas before passing through the catalyst, i.e., the change of an oxygen partial pressure, is moderated by passing the exhaust gas through the catalyst. Specifically, as shown in FIG. 4A, irrespective of whether the air/fuel ratio of the exhaust gas before passing through the catalyst is rich or lean, the oxygen partial pressure of the exhaust gas after passing through the catalyst is reduced. The amplitude of the output voltage wave form of the oxygen sensor downstream from the catalyst is reduced. However, when the purifying efficiency of the catalyst is lowered, the oxygen storage capability of the catalyst is lowered. Therefore, even after the exhaust gas is passed through the catalyst, the change of the air/fuel ratio to the rich/lean side in the exhaust gas before passing through the catalyst is kept as it is and fails to be moderated. Specifically, as shown in FIG. 4B, the change of the air/fuel ratio to the rich/lean side in the exhaust gas before passing through the catalyst results in the change in the oxygen partial pressure of the exhaust gas after passing through the catalyst. The amplitude of the output voltage wave form of the oxygen sensor downstream from the catalyst is increased in the same manner as in the front oxygen sensor. Therefore, the deterioration degree of the oxygen storage capability of the catalyst can be detected by tracing the change of the output voltage of the oxygen sensor downstream from the catalyst and judging whether the amplitude of the output voltage wave form is large or small.

Additionally, in the aforementioned first or second catalyst deterioration detecting method, the oxygen sensor downstream from the catalyst may be used only for detecting the deterioration of the catalyst.

However, in a case where the deterioration degree of the catalyst for an engine using compressed natural gas or CNG fuel or the like is estimated in the same manner as the first or second catalyst deterioration detecting method, defects arise and the catalyst deterioration cannot be detected.

Specifically, when the purifying ratio of the catalyst is high, that is, even when the catalyst has not deteriorated, in the first catalyst deterioration detecting method, as shown in FIG. 3C, the reversing time of the output voltage of the oxygen sensor downstream from the catalyst is shortened in a certain temperature range irrespective of the deterioration state of the catalyst, because of the influence of a large amount of methane contained in the CNG fuel. Furthermore, in the second catalyst deterioration detecting method, as shown in FIG. 4B, the problem is that the amplitude of the output voltage wave form of the oxygen sensor downstream from the catalyst changes in the same manner as when the catalyst has deteriorated.

More specifically, since the methane contained in the exhaust gas is not sufficiently burnt even after passing through the catalyst, unburnt methane remains. When a detection electrode of the oxygen sensor downstream from the catalyst has a low temperature, however, the unburnt methane does not react with oxygen in the vicinity of the detection electrode. Therefore, no change occurs in the oxygen partial pressure, and the output voltage of the oxygen sensor downstream from the catalyst is not influenced.

However, when the temperature of the detection electrode of the oxygen sensor downstream from the catalyst reaches or exceeds a certain temperature, in the first catalyst deterioration detecting method, the unburnt methane causes a burning reaction with the oxygen on the detection electrode. Therefore, a difference in oxygen concentration between a reference electrode and the detection electrode changes in accordance with the concentration of methane. If the amount of methane exceeds the stoichiometric amount at a time when methane causes a burning reaction with the oxygen in the exhaust gas, the oxygen of the detection electrode is drawn away. Therefore, the output voltage is largely raised. If the amount of methane is equal to or less than the stoichiometric amount, no oxygen at the detection electrode is drawn away. Therefore, the output voltage is lowered. As a result, the reversing cycle depends on the methane concentration, but does not depend on the oxygen storage capability of the catalyst. The burning reaction becomes significant as the temperature of the detection electrode rises. Therefore, the reversing time of the oxygen sensor downstream from the catalyst becomes shorter as the temperature of the detection electrode rises.

Moreover, when the temperature of the detection electrode of the oxygen sensor downstream from the catalyst reaches or exceeds a certain temperature, in the second catalyst deterioration detecting method, the unburnt methane causes a burning reaction with the oxygen at the detection electrode. Since the oxygen at the detection electrode is drawn away, a difference in the oxygen partial pressure is generated. The output voltage is largely raised in accordance with the methane concentration, i.e., when the methane concentration is high or the air/fuel ratio is rich. For this reason, even if the catalyst is normal, the output voltage of the oxygen sensor downstream from the catalyst changes in accordance with the change of the air/fuel ratio toward rich/lean. Therefore, the catalyst deterioration cannot be detected.

As aforementioned, in the case where the deterioration degree of the catalyst for the engine using the CNG fuel or the like is detected based on an output signal of the oxygen sensor downstream from the catalyst, a problem remains unsolved in that the output voltage of the oxygen sensor downstream from the catalyst is not stabilized because of the burning reaction of the oxygen in the vicinity of the detection electrode with the unburnt methane.

SUMMARY OF THE INVENTION

Wherefore, an object of the present invention is to provide an oxygen sensor which is disposed downstream from a catalyst for purifying exhaust gas from an internal combustion engine and which can suppress an influence of unburnt hydrocarbon on an output voltage.

To attain this and other objects, the present invention provides an oxygen sensor which has a detection electrode on one face of a solid electrolytic body having an oxygen ion conductivity and a reference electrode on the other face thereof and which is disposed downstream from a catalyst for purifying an exhaust gas from an internal combustion engine using fuel which contains hydrocarbon having a ratio of hydrogen to carbon of 3:1 or more, i.e., $H/C \geq 3$.

The oxygen sensor is provided with an output inhibitor for controlling an output voltage, which changes in accordance with the concentration of hydrogen or carbon monoxide, in such a manner that the output voltage, which depends on the concentration of hydrocarbon, is prevented from exceeding a reference level by which it is determined whether an air/fuel ratio is rich or lean.

As the solid electrolytic body having the oxygen ion conductivity, ceramics such as a ceramic mainly composed of zirconium oxide are preferable. The solid electrolytic body can be obtained by mixing raw-material powder of zirconium oxide or the like with sintering assistant powder of yttrium oxide, silicon oxide, magnesium oxide or the like, granulating the mixture, forming a predetermined configuration, calcining as the case may be, and subsequently sintering.

As aforementioned, when the solid electrolytic body is prepared, after mixing and granulating, the predetermined configuration, e.g., a cup or bottomed cylindrical configuration, a plate configuration or the like is formed. The forming is performed in a rubber pressing or by another pressing method, a thick-film or other laminating method, or the like.

The detection electrode and the reference electrode formed on the solid electrolytic body are each formed as a thin-film electrode of a conductive material mainly composed of a noble metal element having a catalyst action to promote the burning of hydrocarbon or another unburnt gas, e.g., at least one component selected from the group consisting of platinum, rhodium, palladium, ruthenium, osmium, iridium and the like. These electrodes can be formed in a plating method, a sputtering method, a pyrolysis of metal-salt, or the like.

The oxygen sensor of the invention is suitable for detecting the deterioration of the catalyst for the internal combustion engine which uses the fuel containing hydrocarbon with the hydrogen/carbon ratio of 3:1 or more. Even after passing through a normal catalyst, the hydrocarbon with the hydrogen/carbon ratio of 3:1 or more represented by methane remains unburnt in the catalyst, and reaches the oxygen sensor disposed downstream from the catalyst as it is. When the temperature of the detection electrode of the oxygen sensor is sufficiently high, the hydrocarbon is burnt around the detection electrode. Therefore, the oxygen around the detection electrode is consumed, thereby lowering the oxygen partial pressure and raising the output voltage.

Here, even if the exhaust gas having passed through the normal catalyst contains unburnt hydrocarbon, the unburnt hydrocarbon should have no influence on the determination of the rich/lean state. In this respect, according to the oxygen sensor of the invention, the output voltage dependent on the fuel containing hydrocarbon (like methane) is less than the reference level by which the air/fuel ratio is determined to be rich or lean. Therefore, even if the output voltage is raised by burning the unburnt hydrocarbon in the vicinity of the detection electrode, the output voltage does not exceed the reference level. The unburnt hydrocarbon has no influence on the determination of the rich/lean state. Here, the reference level is preferably determined in a range of 400 to 600 mV. If the reference level is outside the range, the center of the amplitude of the output voltage wave form of the oxygen sensor has deviated. Since the reversing cycle becomes irregular, deterioration cannot be easily detected with sufficient precision.

According to the invention, in the oxygen sensor, the influence of the unburnt hydrocarbon on the output voltage can be suppressed. As a result, deterioration of the catalyst can be effectively detected with high precision. Specifically, even in either the first or second catalyst deterioration detecting method described above, deterioration of the catalyst can be detected with high precision. Moreover, the engine can be controlled based on the output voltage of the oxygen sensor.

Additionally, the output inhibitor of the invention may function by inhibiting the catalyst activity of the detection electrode itself, or may function by generating a difference in the rate gasses such as hydrogen, carbon monoxide and hydrocarbon reach the detection electrode. In the former case, impurities such as gold, silver, copper, lead and the like may be added as dopants in the detection electrode. The catalyst activity point of a detection electrode surface may be decreased by heating the detection electrode to a temperature higher than the usual operation temperature of the oxygen sensor, for example, to 1200° C. or higher, or by forming the detection electrode of a thinner plating film as compared with a typical oxygen sensor. The detection electrode with a low catalyst activity may be formed by plating with platinum containing a slight amount of impurities such as gold, silver, copper, lead and the like. Furthermore, the detection electrode may be formed of one of the impurities, mentioned above, and a material having a low catalyst activity such as iridium and the like. In the latter case, the influence of the hydrocarbon on the oxygen sensor output may be relatively decreased by thickening a porous protective layer on the detection electrode or lowering the porosity of the porous protective layer to increase the diffusion resistance of the detected gas component to the detection electrode. Moreover, the contribution of the hydrocarbon to the oxygen sensor output may be inhibited by reducing the size or the number of vent holes in a protector which covers the periphery of the detecting element or oxygen sensor to allow the protector to have gas election properties.

On the other hand, when the oxygen sensor of the invention only satisfies the condition that the output voltage dependent on the hydrocarbon concentration is less than the reference level for determining the air/fuel ratio to be rich or lean within the sensor's active temperature, catalyst deterioration is sufficiently detected. Moreover, in this case, the engine can be sufficiently controlled based on the output voltage of the oxygen sensor disposed downstream from the catalyst. Here, the sensor's active temperature is a temperature which can be appropriately determined in accordance with a system incorporating the oxygen sensor and which corresponds to a sensor impedance set sufficiently low relative to an impedance on a system measurement side. Specifically, for example, when the measurement-side impedance is 500 kΩ to 1 MΩ, the sensor impedance is set to 50 kΩ to 100 kΩ.

Furthermore, in the oxygen sensor of the invention, the actual operation temperature ranges to, for example, 900° C. However, if the output voltage dependent on the hydrocarbon concentration is less than the reference level at 400° C. or a higher temperature, that temperature is sufficient and preferable for the detection of the catalyst deterioration and for the control of the engine based on the output voltage of the oxygen sensor disposed downstream from the catalyst. At 400° C. or lower temperatures, the detection electrode cannot be sufficiently activated because of the change in nature caused by long-term use. In this case, there is a disadvantageous possibility in the first catalyst deterioration detecting method that the reversing cycle will not be accelerated because of a response delay or that reversing will not be performed because of an insufficient output. There is a disadvantageous possibility in the second catalyst deterioration detecting method that the output voltage will become substantially constant regardless of catalyst deterioration and that the deterioration will not be detected. The catalyst deterioration is detected in a predetermined operation state. The oxygen sensor temperature ranges, for example, from 400 to 600° C. in accordance with the operation state. Therefore, the aforementioned conditions are preferably satisfied in the predetermined operation state.

Moreover, in the oxygen sensor of the invention, the detection electrode is mainly composed of a noble metal element which has a catalytic action to promote the burning of unburnt gas of the hydrocarbon-containing fuel, and has, at least on its surface, at least one element selected from the group consisting of silver, copper, gold and lead. This composition is preferable for obtaining the effects of the invention. The detection electrode can be manufactured, for example, by dipping the detection electrode into an aqueous solution of a metal salt at a predetermined concentration and subsequently pyrolyzing the metal salt. Examples of the metal salt include silver salt, copper salt, gold salt and lead salt. The inactivity of the detection electrode changes in accordance with the concentration of the aqueous solution of metal salt, but the conditions of the invention can be satisfied by appropriately setting the concentration to, for example, 0.05 to 0.5 mol/l.

Furthermore, according to the oxygen sensor of the invention, in the detection electrode, the average particle size of the noble metal element is 2 μm or more, which is preferable for obtaining the effects of the invention. The detection electrode can be manufactured by sintering the detection electrode mainly composed of the noble metal element at a temperature higher by, for example, 100 to 300° C. than usual.

Additionally, the oxygen sensor of the invention is preferably provided with the following two characteristics:

(1) the output voltage does not exceed the reference level under the condition that the sensor temperature is 400° C. in an atmosphere containing 3000 ppm of methane, 1200 ppm of oxygen, with the rest being non-combustible gas; and (2) the output voltage exceeds the reference level under the condition that the sensor temperature is 400° C. in an atmosphere containing 3300 ppm of hydrogen, 1000 ppm of oxygen, with the rest being non-combustible gas.

In the above (1), the methane concentration in the atmosphere is 3000 ppm, which is equal to or more than the maximum concentration of hydrocarbon in the actual exhaust gas having passed through the catalyst of the internal combustion engine using the methane-containing fuel. Specifically, if the oxygen sensor is sufficiently operated with this concentration, there is no problem about the detecting of deterioration. Moreover, no problems will arise if the engine is controlled based on the output voltage of the oxygen sensor disposed downstream from the catalyst.

Furthermore, in the above (1), the oxygen concentration in the atmosphere is 1200 ppm, which is a properly set value equal to or less than the stoichiometric amount at which the total amount of methane can be burnt. In a case where oxygen is supplied exceeding the stoichiometric amount, the oxygen partial pressure cannot be sufficiently reduced because of the presence of surplus oxygen even if the total amount of methane is burnt in the vicinity of the oxygen sensor detection electrode. Additionally, the output voltage is not generated in some cases. In this case, the influence of methane cannot be precisely evaluated.

Moreover, in the above (1), the point where the output voltage does not exceed the reference level is defined under the condition described above. Therefore, in a case where the purifying efficiency of the catalyst is normally high, even if the output voltage is raised by the influence of methane, the value of the output voltage does not exceed the reference level. Consequently, the determination of the air/fuel ratio to be rich or lean is prevented from being influenced by the unburnt hydrocarbon.

On the other hand, in the above (2), the output voltage needs to be equal to or higher than the reference level under the conditions that the sensor temperature is 400° C. in an atmosphere containing 3300 ppm of hydrogen, 1000 ppm of oxygen, with the rest being non-combustible gas. If the activity of the oxygen sensor detection electrode drops so as to become inactive not only to methane but also to hydrogen, the deterioration of the catalyst of the internal combustion engine using the fuel containing hydrocarbon with the hydrogen/carbon ratio of 3:1 or more cannot be detected. Therefore, the minimum activity of the detection electrode necessary for the detection of the catalyst deterioration is defined. Furthermore, if the detection electrode has such an activity, there is no problem with engine control based on the output voltage of the oxygen sensor disposed downstream from the catalyst. Additionally, the concentrations of hydrogen and oxygen are set in such a manner that in a case of a reaction between hydrogen and oxygen, hydrogen becomes a surplus.

It is preferable that the oxygen sensor of the invention is provided with the above characteristics (1) and (2) even after the oxygen sensor is exposed to the exhaust gas of the internal combustion engine using the hydrocarbon-containing fuel with the hydrogen/carbon ratio of 3:1 or more at 900° C. for 1000 hours. A durability test in which the exposure to exhaust gas is performed at 900° C. for 1000 hours is typical for automobile oxygen sensors. If the characteristics are unchanged even after the test, the oxygen sensor can be actually operated over a long period with high reliability. Additionally, parts do not need to be replaced frequently. In this case, when the detection electrode is mainly composed of the noble metal element having the catalytic action to promote the burning of unburnt gas of the hydrocarbon-containing fuel, and has at least one element selected from the group consisting of silver, copper and gold, at least on its surface, then the detection electrode is provided with the above characteristics (1) and (2) as initial characteristics at the time of manufacture. Moreover, the characteristics will be maintained even after the durability test.

BRIEF DESCRIPTION OF THE DRAWINGS

FIG. 2 is a graph showing the relationship between a sensor temperature and a sensor output;

DETAILED DESCRIPTION OF THE PREFERRED EMBODIMENTS

Preferred embodiments of the present invention will be described.

Figure 1A:
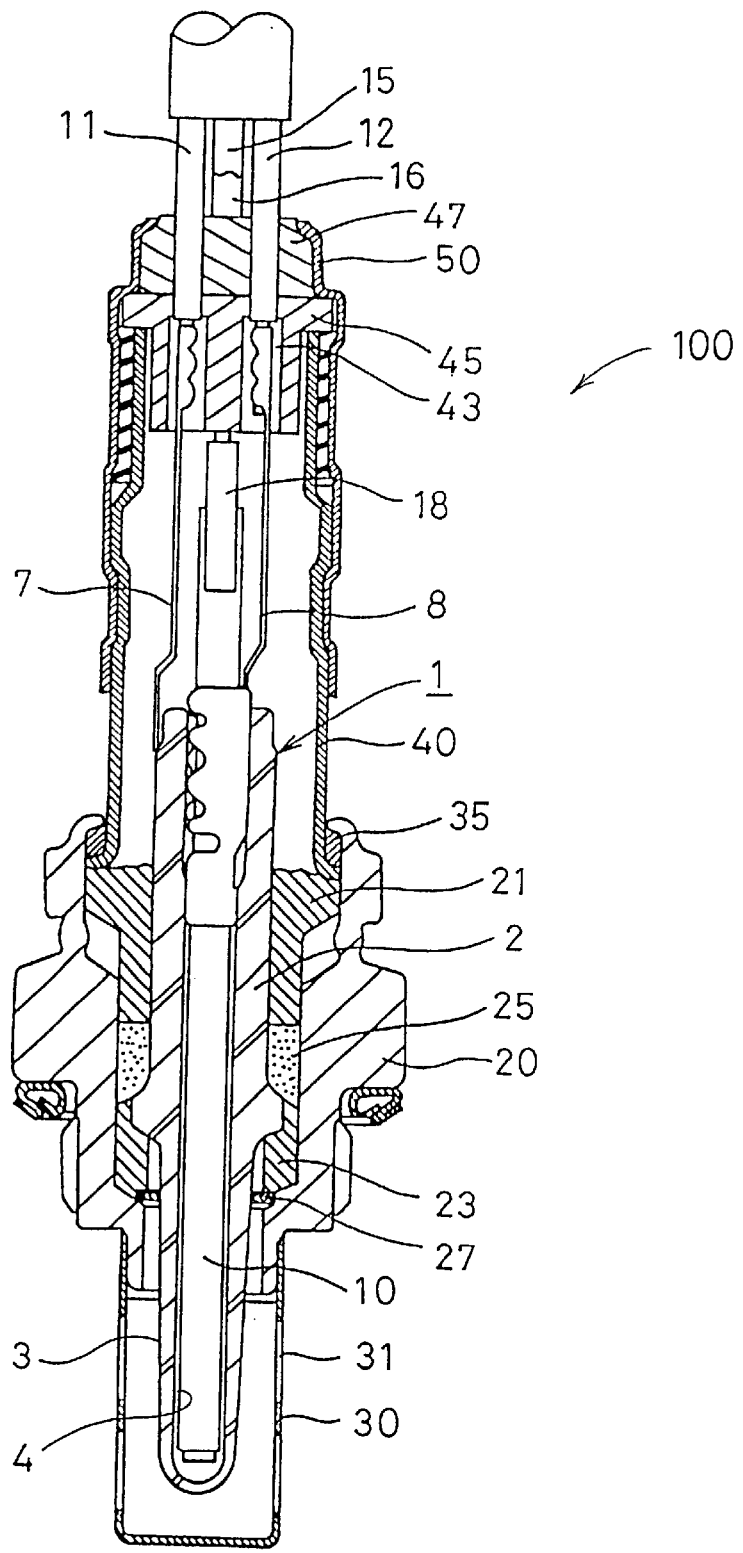
FIG. 1A is a sectional view showing the whole of an oxygen sensor embodying the invention.

As shown in FIG. 1A, a oxygen sensor 100 comprises a detection element 1, ceramic heater 10, a metal shell 20, protective cap 30, an inner barrel 40, an outer barrel 50, and the like. The bar-shaped ceramic heater 10, which is for heating and activating the detection element 1, is inserted in the inside space of the detection element 1. The detection element 1, which is surrounded by cylindrical ceramic holding elements 21, 23, talc powder 25, a packing 27, and the like, is disposed inside the metal shell 20 composed of a heat resisting metal. On the lower part of the metal shell 20, a protective cap 30 which is provided with a hole 31 in order to let in a gas to be detected is mounted in such a manner that the cap covers the end portion of the detection element 1. On the upper part of the metal body 20, the inner barrel 40 composed of heat resisting metal is mounted with an intervening O-ring 35 in such a manner that the inner barrel 40 covers the upper part of the detection element 1 and the ceramic heater 10, and on the upper part of the inner barrel 40 is attached the outer barrel 50 composed of a heat resisting metal. A ceramic separator 45 and a grommet rubber 47 are disposed between the inner barrel 40 and the outer barrel 50 in order to prevent water and the like from getting into the inside of the oxygen sensor 100. Lead wires 11, 12 for taking signals from a detection electrode 3 and a reference electrode 4, which constitute the detection element 1, are connected to connecting terminals 7, 8 of the detection element 1. A connecting terminal 18 of the ceramic heater 10 is connected to lead wires 15, 16 for providing the ceramic heater 10 with electricity. The lead wires 11, 12 as well as the lead wires 15, 16 pass through holes 43 in the ceramic separator 45 then the grommet rubber 47, and extend to the outside.

Figure 1B:
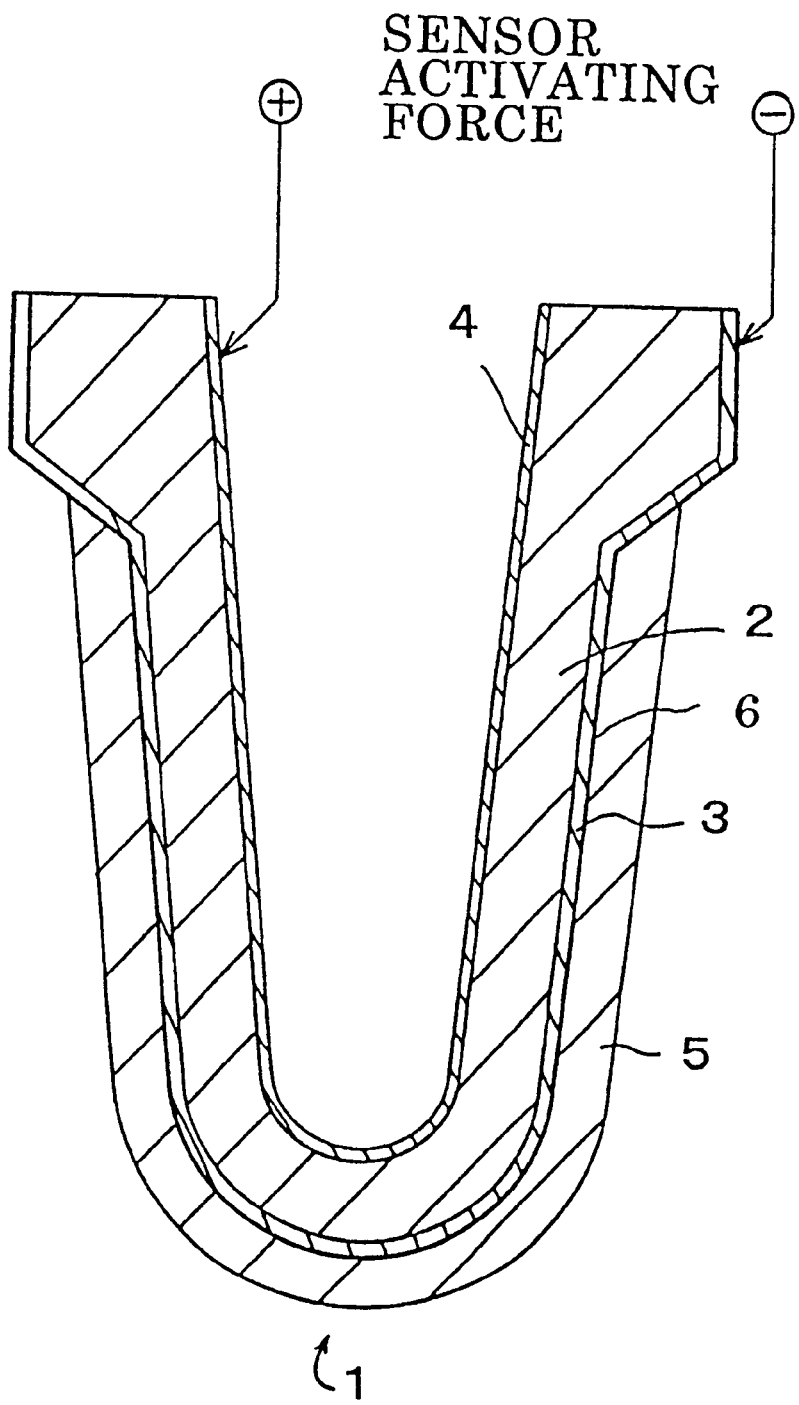
FIG. 1B is an enlarged sectional view of a detection element which is the main part of an oxygen sensor.
Figure 3A:
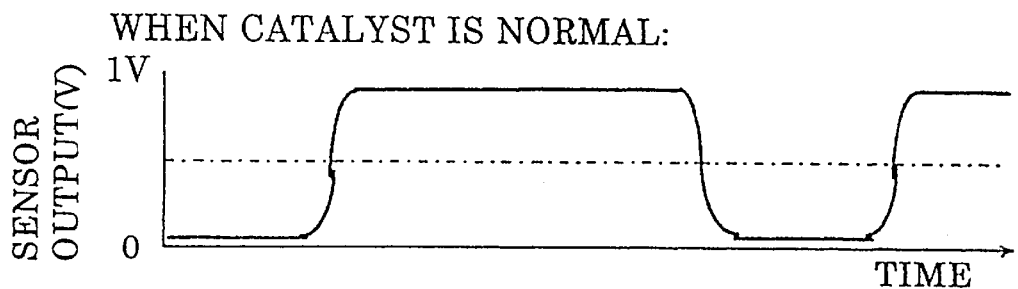
FIGS. 3A, 3B and 3C are explanatory views of a first catalyst deterioration detecting method by an oxygen sensor disposed downstream from a catalyst.
Figure 3B:
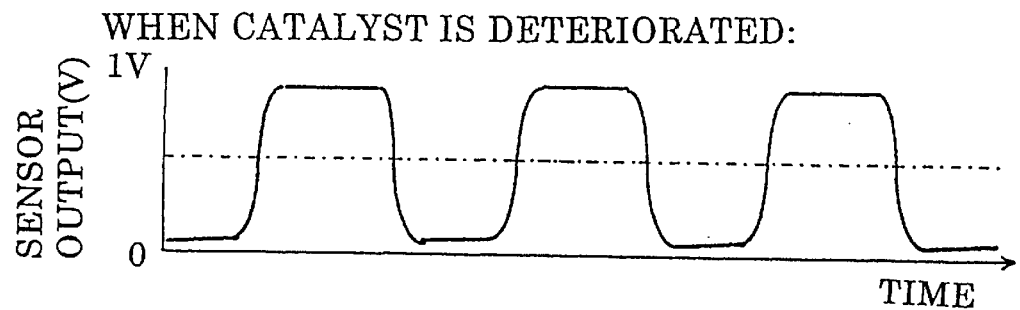
Figure 3C:
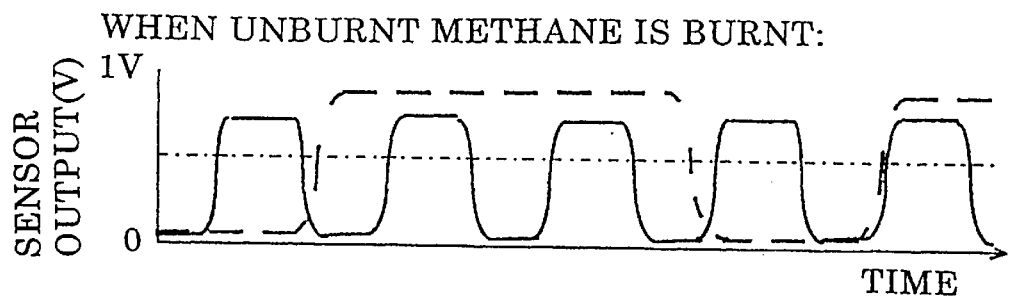
Figure 4A:
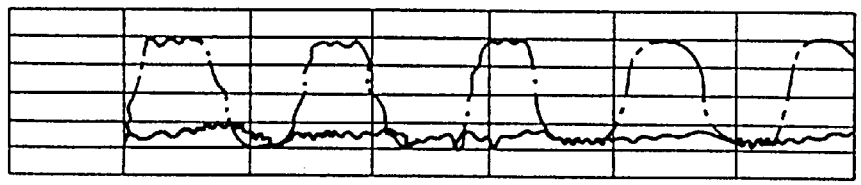
FIGS. 4A and 4B are explanatory views of a second catalyst deterioration detecting method by the oxygen sensor disposed downstream from the catalyst.
Figure 4B:
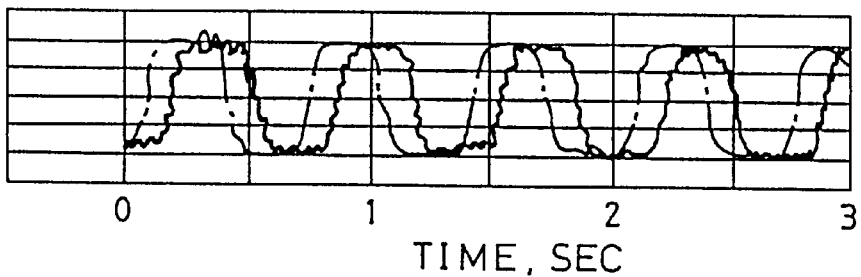

As shown in FIG. 1B, the detection element 1 comprises a cup-shaped ceramic body 2, the detection electrode 3 provided on an outer periphery of the ceramic body 2, the reference electrode 4 provided on the inner periphery of the ceramic body 2, and a protective layer 5 provided on an outer periphery of the detection electrode 3. On the surface of the detection electrode 3, a doped layer 6 having the function of inhibiting the output voltage which depends on the concentration of hydrocarbon contained in an exhaust gas from causing the output voltage to exceed the reference level by which it is determined whether an air/fuel ratio is one of rich and lean is formed.

Next, a method of manufacturing the oxygen sensor 100 will be explained.

FIRST EXAMPLE

After blending $Y_2O_3$ having a purity of 99% or more with $ZrO_2$ having a purity of 99% or more in the proportion of 5 mol to 100 mol and wet-mixing the mixture, calcining was performed at 1300° C. Water was applied to the calcined material. Subsequently, after grinding in a ball mill, water-soluble binder was applied, and granulation was performed via a spray-drying method.

The granulated material was formed into a cup or bottomed cylindrical configuration using a rubber pressing method, and ground with a grindstone. Subsequently, by sintering the formed material at 1500° C. for three hours, a zirconia ceramic body was obtained. A platinum thin film having a thickness of 1 to 2 $\mu$m was formed on the exterior periphery of the ceramic body in an electroless plating method to form a detection electrode. Thereafter, the platinum thin film was thermally treated in an atmospheric environment at 1200° C. for 90 minutes. Thereby, the denseness of the platinum thin film constituting the detection electrode was enhanced and stabilized.

Subsequently, the detection electrode of the ceramic body only was dipped in a silver nitrate aqueous solution of 0.1 mol/l at room temperature for ten seconds, and heated at 800° C. for 60 minutes in the atmospheric environment to pyrolyze silver nitrate.

Subsequently, a platinum reference electrode was formed on the inner periphery or the ceramic body in the electroless plating method to form a thickness of 1 to 2 $\mu$m.

In order to protect the silver-doped detection electrode, a protective layer of spinel powder of magnesium aluminate with a thickness of about 200 $\mu$m was formed on the surface of the detection electrode in a plasma spray coating method.

By the exposure to combustion gas and through aging, a detection element was formed as shown in FIG. 1B. The detection element was set into a metal case together with a cylindrical heater, to complete an oxygen sensor for a CNG engine.

As a result of an Auger analysis on the surface of the detection electrode, before the protective layer of spinel powder was formed, the presence of silver was confirmed. On the other hand, after an about 100 Å thick portion of a metal-particle surface layer forming the surface of the detection electrode was removed by an ion sputtering method, the Auger analysis was performed in the same manner. In the ion sputtering method, argon ion was radiated from a differential exhaust type micro-beam ion gun for several seconds with the ion energy being 3 kV. The result was that no silver was found. Therefore, in the case where the detection electrode formed through plating is dipped in the silver compound solution to impregnate the detection electrode with silver, it is judged that silver is present only in the surface layer.

In the case where the detection electrode was completely melted with aqua regia, heated to evaporate the acid, and an ICP spectral analysis was conducted to determine the concentration of silver, 0.029 μg of silver per 1 $mm^2$ of the detection electrode was present. This corresponds to a dopant to oxidation catalyst material ratio of 0.08%.

SECOND EXAMPLE

An oxygen sensor was prepared in the same manner as in the first example, except that a detection electrode was dipped in a silver nitrate aqueous solution of 0.5 mol/l.

THIRD EXAMPLE

An oxygen sensor was prepared in the same manner as in the first example, except that a detection electrode was dipped in a gold cyanide aqueous solution of 0.05 mol/l.

FOURTH EXAMPLE

An oxygen sensor was prepared in the same manner as in the first example, except that a detection electrode was dipped in a copper acetate aqueous solution of 0.5 mol/l.

FIFTH EXAMPLE

An oxygen sensor was prepared in the same manner as in the first example, except that a detection electrode was dipped in a lead acetate aqueous solution of 0.01 mol/l.

SIXTH EXAMPLE

An oxygen sensor was prepared in the same manner as in the first example, except that the dipping of the detection electrode in the silver nitrate aqueous solution and the subsequent heating treatment at 800° C. were omitted, the temperature of the atmospheric heat treatment after forming the detection electrode was raised from 1200° C. to 1400° C. to advance the sintering of the platinum forming the detection electrode, and the crystal grain diameter was set to 3.0 μm.

First Comparative Example

An oxygen sensor was prepared in the same manner as in the first example, except that the dipping of the detection electrode in the silver-nitrate aqueous solution and the subsequent heating treatment at 800° C. were omitted. In the first comparative example, the detection electrode does not contain a metal selected from the group consisting of silver, copper, gold and lead, and its crystal grain diameter is 1.6 μm, as in a conventional oxygen sensor.

Performance Evaluation Test

The oxygen sensors of the first to sixth examples and the first comparative example were exposed to the atmosphere containing 3000 ppm methane, 1200 ppm oxygen, 9% carbon dioxide and the rest nitrogen. The output voltage of each oxygen sensor was monitored while changing a voltage applied to a cylindrical heater. Thereby, the relationship between a detection-electrode surface temperature, i.e., a sensor temperature or chip temperature, and the sensor output voltage was measured. The composition of the atmosphere was determined by referring to the actual exhaust gas composition of the CNG engine.

Moreover, the oxygen sensors were exposed to the atmosphere containing 3300 ppm hydrogen, 1000 ppm oxygen and the rest nitrogen, and the output voltage of each oxygen sensor was measured at the sensor temperature of 400° C.

Furthermore, to test the durability of each oxygen sensor, after each oxygen sensor was exposed to the engine exhaust gas at 900° C. for 1000 hours, measurement was performed in the same manner. The results are shown in Table 1 and the graph of FIG. 2.

The reference level for determining the air/fuel ratio to be rich or lean was 500 mV, and the deterioration detecting temperature was 400° C.

TABLE 1

| | OXYGEN SENSOR OUTPUT (mV) ON EACH CONDITION | | | | | | | |
|---|---|---|---|---|---|---|---|---|
| | $CH_4$—CONTAINING GAS | | | | | | $H_2$—CONTAINING GAS | |
| | INITIAL | | | AFTER DURABILITY TEST | | | INITIAL | AFTER DURABILITY TEST |
| TEMP (° C.) | 200 | 400 | 600 | 200 | 400 | 600 | 400 | 400 |
| EXAMPLE 1 | 50 | 180 | 450 | 80 | 180 | 500 | 850 | 860 |
| EXAMPLE 2 | 50 | 100 | 150 | 60 | 120 | 200 | 860 | 870 |
| EXAMPLE 3 | 150 | 210 | 500 | 160 | 230 | 520 | 900 | 910 |
| EXAMPLE 4 | 60 | 110 | 170 | 70 | 130 | 210 | 880 | 870 |
| EXAMPLE 5 | 130 | 150 | 400 | 150 | 720 | 900 | 890 | 890 |
| EXAMPLE 6 | 200 | 350 | 900 | 180 | 340 | 880 | 900 | 880 |
| COMPAR. EXAMPLE 1 | 250 | 950 | 920 | 240 | 930 | 900 | 950 | 900 |

As clearly seen from Table 1 and FIG. 2, when the first to fourth examples are exposed to methane-containing gas, in the initial state, i.e., before the durability test, the output voltage is 300 mV or less at the chip temperature, i.e., the deterioration detecting temperature of 400° C. Specifically, the output voltage is 100 to 210 mV, which is less than the reference level and hardly changes even after the durability test. In the sixth example, in the initial state or before the durability test, the output voltage is 350 mV at the chip temperature of 400° C. Although the sixth example is slightly less effective, as compared with the first to fourth examples, its output voltage does not exceed the reference level and does not change even after the durability test. Furthermore, as clearly seen from Table 1, when the first to fourth and sixth examples are exposed to hydrogen-containing gas, each output voltage is 850 mV or more, and thus above the reference level, at the chip temperature of 400° C. both in the initial state and after the durability test. The output voltages of the first to fourth and sixth examples are equal to or higher than the reference level against the hydrogen-containing gas either in the initial state or after the durability test, and do not exceed the reference level against the gas containing a sufficient amount of methane. Moreover, in the first to fourth and sixth embodiments, when the concentration of hydrogen and carbon monoxide are changed, the output voltage changes in accordance with the concentration. The results show that each of the oxygen sensors in the first to fourth and sixth examples can be practically used for a long period as the oxygen sensor disposed downstream from the catalyst for the CNG engine.

Furthermore, as clearly seen from Table 1 and FIG. 2, in the fifth example in which lead is doped in the detection electrode, the output voltage is 300 mV or less, specifically 150 mV which is below the reference level, at the chip temperature of 400° C. against the methane-containing gas in the initial state. After the durability test, however, the output voltage exceeds the reference level and reaches 720 mV at the same temperature. Moreover, as clearly seen from Table 1, the output voltage is 890 mV, and thus above the reference level, at the chip temperature of 400° C. against the hydrogen-containing gas both in the initial state and after the durability test. Therefore, it can be concluded that the oxygen sensor of the fifth example can be practically used for only a short period as the oxygen sensor downstream from the CNG engine catalyst.

In the first comparative example, impurities such as silver are not doped in the detection electrode, and the crystal grain diameter of platinum is less than 2 μm. In a conventional oxygen sensor like this, when the chip temperature is 400° C. or higher, the output voltage reaches 950 mV above the reference level against the methane-containing gas in the initial state. It is seen that the oxygen sensor of the first comparative example is not suitable as the oxygen sensor downstream from the CNG engine catalyst.

In the first and fifth examples, the detection electrode before being provided with the protective layer of spinel powder was completely melted with an aqua regia. The treatment liquid was analyzed with an ICP spectral analysis to quantitatively analyze the doped metal element. The concentration of the treatment liquid of the fifth example was a tenth part of that of the first example, but the doped amount of the fifth example was substantially equal to that of the first example. The doped amount of the fifth example was substantially the same as the first example, and after melting the electrode with aqua regia, heating to evaporate the acid and conducting ICP spectral analysis, resulted in 11 μg Pb to 13 mg of Pt, or a dopant to oxidation catalts mataerial ration of 0.08%.

Therefore, it can be judged that the difference in durability between the first and fifth examples are caused by the metal dopant, not by a difference in the dopant amount.

The invention is not restricted to the embodiments described above, and can be varied within the scope of the invention as defined by the appended claims.

What is claimed is:

1. An oxygen sensor disposed downstream from a catalyst for purifying an exhaust gas from an internal combustion engine fuel, said fuel containing hydrocarbon having a ratio of hydrogen to carbon of at least 3:1, an output voltage of the oxygen sensor varying according to the concentration of oxygen and at least one of hydrogen, carbon monoxide and hydrocarbon, said oxygen sensor comprising:

a reference electrode;

a solid electrolytic body composed of material having an oxygen ion conductivity, said reference electrode disposed on an inner periphery of said electrolytic body; and a detection electrode disposed on an outer periphery of said electrolytic body, said detection electrode having an output inhibiting means for controlling an output voltage of said oxygen sensor, said output inhibiting means inhibiting the voltage generated by the presence of hydrocarbon from exceeding a reference level which would otherwise be exceeded in the presence of the hydrocarbon, said reference level corresponding to a level for determining whether an air/fuel ratio is one of lean and rich.

2. The oxygen sensor according to claim 1, wherein the output inhibiting means inhibits the output voltage within the range of a sensor active temperature.

3. The oxygen sensor according to claim 1, wherein the output inhibiting means inhibits the output voltage at a sensor temperature of at least 400° C.

4. The oxygen sensor according to claim 1 wherein the reference level is in a range between about 400 mV to about 600 mV.

5. The oxygen sensor according to claim 1, wherein the detection electrode is mainly composed of a noble metal which has a catalytic action to promote burning of any unburnt hydrocarbon-containing fuel.

6. The oxygen sensor according to claim 5, wherein the noble metal has at least on its surface, at least one element selected from the group consisting of silver, copper, gold and lead.

7. The oxygen sensor according to claim 1, wherein the detection electrode is formed by plating and composed mainly of a noble metal which has a catalytic action to promote burning of any unburnt hydrocarbon-containing fuel, and the noble metal element has an average particle diameter of at least 2 μm.

8. The oxygen output sensor according to claim 1, wherein, when the sensor temperature is around 400° C. and in an atmosphere containing 3000 ppm methane, 1200 ppm oxygen, with the remainder being non-combustible gasses, the output voltage is below the reference level; and the output voltage is at least at the reference level when the sensor temperature is around 400° C. and in an atmosphere containing 3300 ppm hydrogen, 1000 ppm oxygen, with the remainder being non-combustible gasses.

9. The oxygen sensor according to claim 1, wherein even after the oxygen sensor is exposed, at 900° C. for 1000 hours, to the exhaust gas from the internal combustion engine using the hydrocarbon-containing fuel with the ratio of hydrogen to carbon of at least 3:1, the oxygen sensor maintains characteristics that the output voltage does not exceed the reference level under the condition that the sensor temperature is 400° C. in the atmosphere containing 3000 ppm methane, 1200 ppm oxygen, with the remainder being non-combustible gasses, and that the output voltage is at least at the reference level under the conditions that the sensor temperature is 400° C. in the atmosphere containing 3300 ppm hydrogen, 1000 ppm oxygen, with the remainder being non-combustible gasses.

10. An oxygen sensor comprising:
   a reference electrode substantially composed of a noble metal;
   a solid electrolytic body composed of material having an oxygen ion conductivity, said reference electrode being disposed on an inner periphery of said electrolytic body; and
   a detection electrode disposed on an outer periphery of said electrolytic body, said detection electrode substantially composed of a noble metal doped with a catalyst inhibitor for inhibiting a catalyst activity such that a voltage generated by the presence of hydrocarbon is prevented from exceeding a reference level which would otherwise be exceeded in the presence of the hydrocarbon, said reference level corresponding to a level for determining whether an air/fuel ratio is one of lean and rich, wherein said catalyst inhibitor is present in an amount of approximately 0.029 $\mu$g per mm$^2$ of surface area of said detection electrode.

11. The oxygen sensor of claim 10, wherein the catalyst inhibitor is a dopant selected from the group comprising gold, silver, copper, and lead.

12. The oxygen sensor of claim 10, wherein said detection electrode is formed by plating and heat-treating said detection electrode to at least 1200° C.

13. The oxygen sensor of claim 10, wherein the detection electrode is made from iridium.

14. The oxygen sensor of claim 10, wherein the noble metal of said reference electrode and said detection electrode, is platinum.

15. An oxygen sensor disposed downstream from a catalyst for purifying an exhaust gas from an internal combustion engine fuel, said fuel containing hydrocarbon having a ratio of hydrogen to carbon of at least 3:1, an output voltage of the oxygen sensor varying according to the concentration of oxygen and at least one of hydrogen, carbon monoxide and hydrocarbon, said oxygen sensor comprising:
   a reference electrode made substantially of a material comprising platinum;
   a solid electrolytic body composed of material having an oxygen ion conductivity, said reference electrode disposed on an inner periphery of said electrolytic body; and
   a detection electrode made of a platinum thin film formed on an exterior surface of said electrolytic body in an electroless plating method, said detection electrode doped with a dopant selected from either silver or lead, said dopant present in an amount of approximately 0.029 $\mu$g per mm$^2$ of a surface of said detection electrode for controlling an output voltage of said oxygen sensor, generated by the presence of hydrocarbon, from exceeding a reference level which would otherwise be exceeded in the presence of the hydrocarbon, said reference level corresponding to a level for determining whether an air/fuel ratio is one of lean and rich.

16. An oxygen sensor comprising:
   a reference electrode substantially composed of a platinum material;
   a solid electrolytic body composed of material having an oxygen ion conductivity, said reference electrode disposed on an inner periphery of said electrolytic body; and
   a detection electrode made of a platinum thin film formed on an exterior surface of said electrolytic body in an electroless plating method, said detection electrode doped with a dopant selected from either silver or lead, said dopant present in an amount of approximately 0.029 $\mu$g per mm$^2$ of a surface of said detection electrode, said dopant for controlling an output voltage of said oxygen sensor, generated by the presence of hydrocarbon, from exceeding a reference level which would otherwise be exceeded in the presence of the hydrocarbon, said reference level corresponding to a level for determining whether an air/fuel ratio is one of lean and rich.

* * * * *